US008652517B2

(12) United States Patent
Entner et al.

(10) Patent No.: US 8,652,517 B2
(45) Date of Patent: Feb. 18, 2014

(54) COATING OF TABLET CORES

(75) Inventors: Reinhard Entner, Breitenbach (AT); Herwig Jennewein, Absam (AT)

(73) Assignee: Sandoz GmbH, Kundl (AT)

( * ) Notice: Subject to any disclaimer, the term of this patent is extended or adjusted under 35 U.S.C. 154(b) by 959 days.

(21) Appl. No.: 11/233,121

(22) Filed: Sep. 22, 2005

(65) Prior Publication Data

US 2006/0034917 A1 Feb. 16, 2006

Related U.S. Application Data

(63) Continuation of application No. 10/130,650, filed as application No. PCT/EP00/11590 on Nov. 21, 2000, now abandoned.

(30) Foreign Application Priority Data

Nov. 23, 1999 (AT) ........................................ 1988/99

(51) Int. Cl.
*A61K 9/20* (2006.01)
*A61K 9/28* (2006.01)

(52) U.S. Cl.
USPC .......................................... 424/464; 427/2.14

(58) Field of Classification Search
USPC .......................................... 424/464; 427/2.14
See application file for complete search history.

(56) References Cited

U.S. PATENT DOCUMENTS

| | | | | |
|---|---|---|---|---|
| 3,185,626 A | * | 5/1965 | Baker | 427/2.2 |
| 3,361,631 A | | 1/1968 | Weinstein | |
| 3,639,564 A | | 2/1972 | Kawata | |
| 3,751,277 A | | 8/1973 | Small et al. | |
| 3,753,767 A | | 8/1973 | Becker | |
| 3,798,054 A | * | 3/1974 | Kawata et al. | 424/479 |
| 4,238,510 A | * | 12/1980 | Cherukuri et al. | 426/5 |
| 4,423,086 A | | 12/1983 | Devos et al. | |
| 4,511,553 A | | 4/1985 | Boesig et al. | |
| 4,840,797 A | | 6/1989 | Boursier | |
| 4,865,851 A | | 9/1989 | Elliot et al. | |
| 4,897,270 A | * | 1/1990 | Deutsch et al. | 424/465 |
| 5,037,845 A | | 8/1991 | Oxford | |
| 5,224,989 A | | 7/1993 | Likarova | |
| 5,882,707 A | | 3/1999 | Saraceni et al. | |
| 6,221,402 B1 | * | 4/2001 | Itoh et al. | 424/494 |

FOREIGN PATENT DOCUMENTS

| | | | |
|---|---|---|---|
| DD | 273000 | 11/1989 | |
| DE | 19503670 | 8/1996 | |
| EP | 169319 | 1/1986 | |
| EP | 220176 B1 | 5/1987 | |
| EP | 0 280 571 | * 8/1988 | ............... A61K 9/22 |
| EP | 595110 | 5/1994 | |
| EP | 722720 | 7/1996 | |
| EP | 803250 | 10/1997 | |
| EP | 0503440 | 5/1998 | |
| GB | 407919 | * 6/1932 | |
| GB | 407 919 | 3/1934 | |
| JP | 55136218 | 10/1980 | |
| JP | 57134414 | 8/1982 | |
| JP | 62005910 | 1/1987 | |
| WO | WO 98/30341 | 7/1998 | |
| WO | WO 99/51210 | 10/1999 | |
| WO | WO 99/65499 | 12/1999 | |

OTHER PUBLICATIONS

Fiedler, "Lexikon der Hilfsstoffe fur Pharmazie, Kosmetik und Angrenzende Gebiete" 4th Edition, pp. 14, 15, 18, 19, 22-25 and 636-639 (1996).
Opposition filed in corresponding European application (Jan. 25, 2010).
Pschyrembel Klinisches Worterbuch, 257th ed., 1994.
J. Controlled Release, vol. 38, 1994, 75-84.
J. Food Composition and Analysis, vol. 15, 2002, 367-377.
Drug Manufacturing Technology Series, vol. 3, Aug. 24, 1999.
Lehrbuch der pharmazeutischen Technologie, Bauer K., 7th ed., 2002.
Eur. J. Pharmaceutics & Biopharmaceutics, vol. 46, 1998, 85-94.
J. Pharmaceutical Sciences, vol. 57, 1968, 1223-1226.

\* cited by examiner

*Primary Examiner* — Aradhana Sasan
(74) *Attorney, Agent, or Firm* — Jeffrey S. Melcher; Manelli Selter PLLC

(57) ABSTRACT

A process for the coating of tablet cores, said tablet core comprising an effective amount of at least one pharmaceutically active compound, comprising spraying a coating solution or suspension comprising a sugar, or a starch, or a mixture of a sugar and a starch onto the tablets or tablet cores with the proviso that film-forming agents in the coating solution or suspension are excluded, to obtain coated tablets, such coated tablets and corresponding coating mixtures.

15 Claims, No Drawings

COATING OF TABLET CORES

This application is a continuation of U.S. patent application Ser. No. 10/130,650, filed Sep. 23, 2002, abandoned, which is a national stage entry under 35 U.S.C. 371 of International of PCT Application No. PCT/EP 00/11590, filed Nov. 21, 2000, abandoned, which in its entirely is herein incorporated by reference. This application claims foreign priority under 35 U.S.C. 119 and 365 to Austrian Patent Application No. 1988/99, filed 23 Nov. 1999.

The present invention relates to coating, e.g. to coating of pharmaceutical tablets/tablet cores.

Pharmaceutical dosage forms for oral application of a pharmaceutically active compound include tablets. For administration of a pharmaceutically active compound in tablet form it often necessary to mask an unpleasant, e.g. bitter, taste of a pharmaceutically active compound. One possibility for taste masking is film-coating with a film which is soluble in gastric juices by use of film-forming agents which results in film-coated tablets. Film-forming agents are usually polymers which form a continuous, elastic and uniform covering, e.g. like a skin, around the tablet core which is at least partially detachable as a continuous layer. Such a film in a film-coated tablet, however, may provide a considerable barrier to the penetration of aqueous fluids into the tablet cores, which is a pre-requisite for disintegration of the tablet core and release of, e.g. sufficient amounts, of the pharmaceutically active compound. Insufficient release of the pharmaceutically active compound may create problems, e.g. such as described for film-coated tablets comprising cefuroxime axetil as a pharmaceutically active compound from which it is known that a very thin layer of a film coating has to be applied to ensure sufficient release. Examination and control of such thin layers is difficult affording special and complex, but non-specific, testing methods (e.g. film bursting test). Varying film thicknesses in different film-coated tablets within the same batch may not be excluded and the same release behaviour of cefuroxim axetil from different film-coated tablets comprising cefuroxime axetil may not be guarantee for each tablet, even if originating from the same production batch.

We have now surprisingly found a process wherein a tablet core comprising a pharmaceutically active compound may be coated without the use of film-forming agents, whilst achieving satisfactory taste masking and avoiding the negative effect of a film coating on the release of the pharmaceutically active compound; and which provides a coated tablet which may directly be administered without further treatment. According to the present invention a thin and complex coating is unnecessary because the coating according to the present invention does not provide a considerable barrier to the penetration of aqueous fluids into the tablet cores, and thus does not affect or prevent the disintegration of the tablet core.

In one aspect the present invention provides a process for the coating of tablet cores, e.g. including a normal tablet core and a dispersible tablet core, said tablet core comprising an effective amount of at least one pharmaceutically active compound, e.g. a pharmaceutically active compound having an unpleasant, e.g. bitter, taste, e.g. a pharmaceutically active compound is selected from antibiotics, such as penicillins, e.g. amoxicillin; e.g. amoxicillin alone or in combination with clavulanic acid; cephalosporins, e.g. cefuroxime axetil; macrolides such as erythromycins; antimigraines, e.g. sumatriptan, or antipsychotics, e.g. olanzapine; comprising spraying a coating solution or suspension comprising a sugar, e.g. including sugars, sugar alcohols; or a starch, e.g. including starch products and starch hydrolysates, or a mixture of a sugar and a starch, onto the tablet cores, with the proviso that film-forming agents in the suspension or solution are excluded, to obtain coated tablets, e.g. which are ready for administration without further treatment.

A pharmaceutically active compound according to the present invention includes all kind of pharmaceutically active compounds, preferably a compound having an unpleasant, e.g. bitter taste, e.g. a compound selected from antibiotics, e.g. including penicillins, e.g. including salts and/or solvates thereof, e.g. including amoxicillin, e.g. in the form of a trihydrate, e.g. amoxicillin alone or in combination with clavulanic acid or salts thereof, such as clavulanic acid in the form of a potassium salt; penicillin V, e.g. including therapeutically active derivatives, oxacillin, cloxacillin, flucoxacillin, dicloxacillin, ampicillin;

cephalosporins, e.g. including salts and/or solvates thereof, such as cefaclor, cefixime, cephalexin, cephradine, cefadroxil, cefroxadine, cefdinir, cefpodoxime proxetil, cefuroxime axetil;

macrolides, e.g. including salts and/or solvates thereof, e.g. including erythromycins, such as erythromycin A, clarithromycin, azithromycin, roxithromycin.

antimigraines, e.g. including salts and/or solvates thereof, e.g. including sumatriptan; e.g. in the form of a hemisulfate, succinate; or antipsychotics, e.g. including salts and/or solvates thereof, e.g. including olanzapine; preferably cefuroxime axetil, cefpodoxime proxetil, amoxicillin, sumatriptan and olanzapine.

A pharmaceutically active compound may be used in any known solid modification; e.g. cefuroxime axetil may be used in amorphous form, crystalline form and in the form of a so solution in a polymer or a solid dispersion on an adsorbent wherein cefuroxime axetil is neither crystalline nor amorphous, e.g. obtainable by removing the solvent of a solution or suspension of cefuroxime axetil and a polymer, or an adsorbent, respectively.

Antibiotics, antimigraines and antipsychotics as described above are disclosed e.g. in The Merck Index, 12th edition, items 7220-7229, 617, 2402, 7230-7232, 7036, 2480, 3134, 62 1962, 1975, 2021, 2032, 1963, 1993, 1971, 1991, 2002, 3720, 8433, 2400, 946, 9172, 6959.

A tablet core as used herein relates to an uncoated tablet, comprising at least one pharmaceutically active compound. A tablet core useful according to the present invention may be in any geometrical form and shape and may be obtained according, e.g. analogously, to a method as conventional. A tablet core may comprise beside the pharmaceutically active compound pharmaceutically acceptable excipients, e.g. including excipients, such as binders, fillers, disintegrators, accelerators, flow conditioners, releasing agents, lubricants, wetting agents, preservatives, colorants, sugar, sugar substitutes, sweeteners, flavouring agents. A tablet core may be obtained as appropriate, e.g. may be obtained by mixing a pharmaceutically active compound with pharmaceutically acceptable excipients, e.g. including granulation, e.g. wet or dry granulation, equalizing (sieving) steps and compressing the mixture obtained. For tablet core production a pharmaceutically active compound may be in any form, e.g. including ungranulated and granulated forms, extruded forms.

A tablet core comprises a tablet core of a normal tablet and a tablet core of a dispersible tablet, i.e. a rapidly disintegrating tablet. A dispersible tablet may e.g. be used for the production of a drink solution or suspension or may be administered as such. Generally dispersible tablets consists of pure tablet cores which are uncoated, e.g. due to the barrier for liquid penetration in case of film-coating which may not allow quick disintegration, e.g. further comprising in the tablet core sweeteners, sugars, flavourants and other ingredients which may e.g. allow a taste masking of an unpleasant, e.g. bitter tasting pharmaceutically active compound.

The coating mixture according to the present invention comprises a sugar, e.g. including one or more sugars, a starch, e.g. including one or more starches; or a sugar and a starch, including one or more sugars and one or more starches. A sugar includes all kind of sugars and compounds having a chemical structure derived from a chemical sugar structure, e.g. sugar alcohols, such as saccharose, lactose, mannitol. A starch includes all kind of starches, and compounds having a chemical structure derived from a starch, e.g. including modified starches, such as potato starch, maize starch, soluble starches, starch hydrolysates, e.g. dextrins, maltodextrin, cyclodextrins. A coating mixture according to the present invention preferably comprises a sugar, e.g. one or more sugars and a starch, e.g. one or more starches. The coating mixture according to the present invention may additionally comprise parting agents, e.g. including talc, pigments, e.g. including titanium oxide, colouring agents, sweeteners, e.g. including aspartame, flavouring agents, wetting agents, e.g. including Texapon®, polyoxyethylene sorbitan fatty acid esters, e.g. including POLYSORBATE 80®, preservatives and lubricants, e.g. siliciumdioxide, e.g. Aerosil® and antifoaming agents, e.g. Simethicone USP. Film-forming agents are excluded. A coating solution or suspension according to the present invention may be obtained according, e.g. analogously, to a method as conventional, e.g. mixing a coating mixture according to the present invention with a liquid which is appropriate for spray coating, e.g. including water, organic, water-miscible solvent (mixture), or a mixture of water and organic water-miscible solvent (mixture). An organic water-miscible solvent (mixture) is a solvent (mixture) appropriate for spray coating e.g. and include a water-miscible solvent (mixture) as conventional.

The tablet cores are coated with the solution or suspension of the coating mixture according to the present invention by spraying, e.g. as appropriate, e.g. according, e.g. analogously, to a method as conventional, e.g. using conventional spraying equipment The solution or suspension of the coating mixture is sprayed onto the tablet cores in an amount sufficient to cover, e.g. uniform, the surface of the tablet cores. The thickness of the coating is not critical, since the coating according to the present invention does not establish a barrier to water penetration of the coated tablet. Preferably the weight of the coat is 20% and less, more preferably 10% and less, e.g. 5% and less, such as 0.5 to 20%, preferably 1 to 15%, of the weight of the coated tablet. It is preferred that the geometrical form or shape of the tablet core before coating is the same in the coated tablet after coating. A coated tablet according to the present invention may have very similar disintegrating characteristics and release characteristics of the pharmaceutically active compound as the tablet core has before coating.

In another aspect the present invention provides a process for the coating of tablet cores, e.g. including a normal tablet core and a dispersible tablet core; said tablet core comprising an effective amount of at least one pharmaceutically active compound, comprising spraying a coating solution or suspension originating from a coating mixture consisting of a sugar, e.g. including sugars, sugar alcohols; or a starch, e.g. including starch products and starch hydrolysates, or a mixture of a sugar and a starch, and optionally of parting agents, and/or pigments, and/or colouring agents, and/or sweeteners, and/or flavouring agents, and/or wetting agents, and/or preservatives and/or lubricants (glidants) and/or antifoaming agents, onto the tablet cores, to obtain coated tablets, e.g. which are ready for administration without further treatment.

Coated tablets obtained according to the present invention are novel.

In another aspect the present invention provides a coated tablet, e.g. including normal tablets and dispersible tablets, e.g. ready for administration without further treatment, comprising an effective amount of at least one pharmaceutically active compound, coated, with a coating mixture consisting of a sugar, e.g. including sugars, sugar alcohols; or a starch, e.g. including starch products and starch hydrolysates, or a mixture of a sugar and a starch, and optionally of parting agents, and/or pigments, and/or colouring agents, and/or sweeteners, and/or flavouring agents, and/or wetting agents, and/or preservatives and/or lubricants and/or antifoaming agents.

A coating mixture used according to the present invention is novel.

In another aspect the present invention provides a coating mixture for the production of coated tablets, e.g. including normal tablets and dispersible tablets; e.g. ready for administration without further treatment, the tablet core of said coated tablet comprising an effective amount of at least one pharmaceutically active compound, wherein the coating mixture consists of a sugar, e.g. including sugars, sugar alcohols; or a starch, e.g. including starch products and starch hydrolysates, or a mixture of a sugar and a starch, and optionally of parting agents, and/or pigments, and/or colouring agents, and/or sweeteners, and/or flavouring agents, and/or wetting agents, and/or preservatives and/or lubricants (glidants) and/or antifoaming agents.

A dispersible tablet comprising a tablet core which comprises a pharmaceutically active compound and which tablet core is coated, are novel. We have found, that the disintegration time of a dispersible tablet core without a coating and of the corresponding tablet core (identical) which is coated with a coating according to the present invention is very similar, e.g. practically the same.

In another aspect the present invention provides a dispersible tablet comprising a tablet core which comprises an effective amount of a pharmaceutically active compound, wherein o said tablet core is coated; e.g. coated with a coating mixture according to the present invention, e.g. and the disintegration time of the uncoated tablet is very similar to that of a corresponding coated tablet, e.g. both tablets containing the same ingredients in the same amounts, e.g. the disintegration time being determined according to standard methods; e.g. according to a method as described in Pharmacopoeias for disintegration tests, e.g. the tablet of which the disintegration time is to be determined is put into water of neutral pH and of a temperature of 20° C. for dispersible tablets or 37° C. for non-dispersible tablets, the tablet disintegration is determined visually and the disintegration time is determined.

A coated tablet core in a dispersible tablet may have several advantages:

- a coating according to the present invention may prevent disintegration of the tablet and release of the active compound already in the mouth of a patient as is possible with uncoated tablets on contact with salvia or another liquid which may be unpleasant for the patient;
- a coated dispersible tablet is better protected from environmental influences than an uncoated tablet which may result in improved stability, higher shelf life and higher purity of the coated tablet, e.g. when storing;
- uncoated dispersable tablets may contain dust, e.g. originating from unavoidable abrasion e.g. during packaging and transport, e.g. said dust comprising the pharmaceutically active compound; e.g. which may be unpleasant on administration; said abrasion and dust may be prevented in a coated dispersible tablet according to the present invention.

dispersible tablet according to the present invention may be used for the production of a drink solution or suspension avoiding the unfavourable behaviour of film-coated tablets which is that a standard film coating, due to its characteristic of forming a continuous skin-like structure, remains in the liquid of the drink solution in the form of continuous pieces of segments of film.

In another aspect the present invention provides the use of a coating mixture according to the present invention in the production of coated tablets, e.g. including normal tablets and dispersible tablets, which comprise in the tablet core an effective amount of at least one pharmaceutically active compound.

In another aspect the present invention provides tablets which contain an active ingredient having a bitter taste, characterised in that they are coated with sugars, sugar derivatives, sugar alcohols and their derivatives, such as saccharose, lactose or mannitol, all starches, starch products, starch derivatives, such as potato starch, soluble starch, and starch hydrolysates, such as dextrins, maltodextrin, cyclodextrins, whereby they may be used alone or in any combination with one another.

In the following examples all temperatures are given in degree Celsius.

General Procedure—Spray Coating

A homogenised suspension comprising a coating mixture is sprayed onto tablet cores until the tablet cores are uniformly covered with the coating. A coated tablet is obtained having the same geometrical shape as the tablet core before coating. The weight of the coating is less than 20%, e.g. less than 10% of the weight of the coated tablet.

EXAMPLE 1

Coated Tablets Comprising Cefuroxime Axetil Granulate
A) Tablet Cores

Per tablet 608 mg of cefuroxime axetil, 243 mg of a polyvinylpyrrolidone polymer (Kollidone VA64®) and 6 mg of sodium-laurylsulphate (Texapon®) are dissolved in a mixture of acetone and water under gently heating. The solution obtained is spray dried and a granulate is obtained which is mixed per tablet with 110 mg of a Na-carboxymethylcellulose (Ac-di-Sol®), 30 mg of siliciumdioxide (Aerosil 200®) and 5 mg of magnesium stearate. The mixture obtained is compacted and the compacted material is broken up and equalised through a sieve. The equalised material obtained is mixed per tablet with 90 mg of mannitol (Pearlitol SD 20), 30 mg of microcrystalline cellulose (Avicel PH 200®), 40 mg of cross-linked polyvinylpyrrolidone (Polyplasdone®), 14 mg of talcum, 3 mg of magnesium stearate, 6 mg of sodium-laurylsulphate (Texapon®), 40 mg of a Na-carboxymethylcellulose (Ac-di-Sol®) and 6 mg of silicium dioxide (Aerosil 200®) and the mixture obtained is compressed to obtain tablet cores.

B) Coating

Tablet cores obtainable as described in example 1 A) are coated with the following coating mixtures (amounts in % (w/w) per total weight of the coating mixture):
1) Mannitol (21.4%), soluble starch (21.4%), silicium dioxide (Aerosil 200®) (2.0%), talcum (31.8%), titanium dioxide (21.4%), Aspartame (2.0%). Mannitol and soluble starch are dissolved in water. The remaining components are suspended in the resulting solution which is homogenised. A homogenised suspension usable for spray-coating is obtained and coating is carried out and results are obtained as described under the General procedure above.
2) Mannitol (32%), soluble starch (20%), talcum (28%), titanium dioxide (18%), aspartame (2.0%). Mannitol and soluble starch are dissolved in water. Talcum, titanium dioxide and aspartame are dispersed in water. The two resulting mixtures are combined and homogenised. A homogenised suspension usable for spray-coating is obtained and coating is carried out and results are obtained as described under the General procedure above.

EXAMPLE 2

Tablet cores obtainable as described in example 1 A) are coated with the following coating mixture (amounts in % (w/w) per total weight of the coating mixture):

Mannitol (60.6%), starch (6.1%), talcum (18.2%), titanium dioxide (12.1%), aspartame (2.6%), sodium-laurylsulphate (Texapon®) (0.4%)

Mannitol and aspartame are dissolved in water, and starch, pre-swollen in water, is stirred into the solution obtained. The resulting mixture is mixed with the remaining ingredients and the mixture obtained is homogenised. A homogenised suspension usable for spray-coating is obtained and coating is carried out and results are obtained as described under the General procedure above.

EXAMPLE 3

Coated Tablets Comprising Cefuroxime Axetil in Amorphous Form
A) Tablet Cores

Per tablet 608 mg of cefuroxime axetil in amorphous form (corresponding to 500 mg cefuroxime), 110 mg of microcrystalline cellulose, 80 mg of Na-Carboxymethylcellulose (Ac-di-Sol®) and 4 mg of magnesium stearate are mixed and the mixture obtained is compacted. The compacted material obtained is broken up and equalised through a sieve.

The sieved material obtained is mixed per tablet with 60 mg of cross-linked polyvinylpyrrolidone polymer (Crospovidone®), 6 mg of silicium dioxide (Aerosil 200®), 20 mg of talcum, 4 mg of magnesium stearate and 9 mg of Sodium-laurylsulphate (Texapon®) and the mixture obtained is compressed to obtain tablet cores.

B) Coating

Tablet cores obtainable as described in example 3 A) are coated with the following coating mixture (amounts in % (w/w) per total weight of the coating mixture):
1. Mannitol (332%), starch (10.0%), lactose (19.9%), talcum (21.2%), titanium dioxide (14.1%), aspartame (1.4%), sodium-laurylsulphate (Texapon®) (0.2%) Mannitol, lactose and aspartame are dissolved in water, and starch, pre swollen in water, is stirred into the solution obtained. The resulting mixture is mixed with the remaining ingredients and the mbiture obtained is homogenised. A homogenised suspension usable for spray-coating is obtained and coating is carried out and results are obtained as described under the General procedure above.
2. Mannitol (26.7%), soluble starch (16.7%), maize starch (16,7%) talcum (22.5%), titaniun dioxide (15%), aspartame (1.6%), simethicone USP (0.8%). Maize starch is pre-swollen in water. Talcum, titanium dioxide, aspartame and simethicor USP are dispersed in the obtained mixture. Mannitol and soluble starch are dissolved in water. The two resulting mixtures are combined and homogenised. A homogenised suspension usable for spray-coatng is obtained and coating is carried out and results are obtained as described under the General procedure above.

EXAMPLE 4

Tablet cores obtainable as described in example 3 A) are coated with the following coating mixture (amounts in % (w/w) per total weight of the coating mixture):

Mannitol (21.8%), soluble starch (21.8%), talcum (32.5%), titanium dioxide (21.8%), aspartame (2.1%)

Mannitol and soluble starch are dissolved in water. The resulting mixture is mixed with the remaining ingredients and the mixture obtained is homogenised. A homogenised suspension usable for spray-coating is obtained and coating is carried out and results are obtained as described under the General procedure above.

EXAMPLE 5

Coated Dispersible Tablets Comprising Amoxicillin Trihydrate

A) Tablet Cores

Per tablet 1163 mg of amoxicillin trihydrate, 57 mg of microcrystalline cellulose and 3 mg of magnesium stearate are mixed and the mixture obtained is compacted. The compacted material obtained is broken up and equalised through a sieve. The sieved material obtained is mixed per tablet with 120 mg of cross-linked polyvinylpyrrolidone polymer (Crospovidone®), 30 mg of talcum, 3 mg of silicium dioxide (Aerosil 200®), 4 mg of magnesium stearate, 2 mg of aspartame and 18 mg of a flavouring agent and the mixture obtained is compressed to obtain tablet cores.

The tablet cores obtained show a disintegration time in water of 1.3 minutes at 20°.

B) Coating

Coating Mixture (Amounts in % (w/w) per Total Weight of the Coating Mixture)

Mannitol (17.9%), soluble starch (17.9%), maltodextrin (17.9%), talcum (26.7%), titanium dioxide (17.9%), aspartame (1.7%)

Mannitol, maltodextrin and soluble starch are dissolved in water. The resulting mixture is mixed with the remaining ingredients and the mixture obtained is homogenised. The homogenised suspension obtained is sprayed onto the tablet cores obtained in step A). Uniform coated tablets are obtained having the same geometrical shape as the uncoated tablet core. The weight of the coating per tablet is less than 10% of the tablet weight. The coated tablets obtained show a disintegration time in water of 1.2 minutes at 20°. The disintegration time is determined according to standard methods as described above.

EXAMPLE 6

Coated Tablets Comprising Sumatriptan in the Form of a Salt with Succinic Acid (Sumatriptan Succinate)

25 mg, 50 mg and 100 mg coated tablet cores comprising the ingedients (mg per tablet) as set out in the TABLE below are prepared by wet granulating, mixing and compressing, according to a standard methods, to obtain tablet cores and coating the tablet cores obtained thus obtained with an aqueous suspension of a coating mixture containing the ingredients as set out in the TABLE below:

TABLE

| CORE | Ingredient | mg/tablet | | |
|---|---|---|---|---|
| | | 100 mg | 50 mg | 25 mg |
| | Sumatriptan succinate | 140.00 | 70.00 | 35.00 |
| | Lactose monohydrate | 116.00 | 58.00 | 29.00 |
| | Microcrystalline cellulose (Avicel 200 ®) | 35.00 | 17.50 | 8.75 |
| | Na-carboxymethylcellulose (Ac-Di-Sol ®) | 4.50 | 2.25 | 1.13 |
| | Magnesium stearate | 4.50 | 2.25 | 1.13 |

| COATING MIXTURE | | Percent weight per total coating |
|---|---|---|
| | Maize starch | 7.1 to 7.2 |
| | Mannitol | 15.3 |
| | Soluble Starch | 15.3 |
| | Lactose monohydrate | 21.2 to 21.4 |

| CORE | | mg/tablet | | |
|---|---|---|---|---|
| | | 100 mg | 59 mg | 25 mg |
| | Polyoxyethylene sorbitan fatty acid (Polysorbate 80 ®) | 3.5 to 3.7 | | |
| | Aspartame | 1.5 | | |
| | Talcum | 21.3 to 21.4 | | |
| | Titanium dioxide | 14.2 to 14.3 | | |
| | Colourant | 0 to 0.5 | | |

Uniform coated tablets are obtained, with a coating weight of ca. 4% of the total coated tablet weight.

EXAMPLE 7

Coated Tablets Comprising Cefpodoxime Proxetil

A) Tablet Cores

Per tablet 260 mg of cefpodoxime proxetil (corresponding to 200 mg cefpodoxime), 42 mg of microcrystalline cellulose, 50 mg of Na-Carboxymethylcellulose (Ac-di-Sol®) and 3 mg of magnesium stearate are mixed and the mixture obtained is compacted. The compacted material obtained is broken up and equalised through a sieve. The sieved material obtained is mixed per tablet with 76 mg of Lactose, 3 mg of silicium dioxide (Aerosil 200®), 3 mg of magnesium stearate and 3 mg of Sodium-laurylsulphate (Texapon®) and the mixture obtained is compressed to obtain tablet cores.

B) Coating

Coating Mixture (Amounts in % (w/w) per Total Weight of the Coating Mixture)

Mannitol (26.5%), soluble starch (39.7%), talcum (18.6%), titanium dioxide (11.9%) aspartame (1.3%/o), simethicone USP (2.0%).

Mannitol and soluble starch are dissolved in water. Talcum, titanium dioxide, aspartame and simethicon USP are dispersed in water. The two resulting mixtures are combined and homogenised. A homogenised suspension usable for spray-coating is obtained and coating is carried out and results are obtained as described under the General procedure above.

The invention claimed is:

1. A process for the coating of dispersible tablet cores, said dispersible tablet core comprising an effective amount of at least one pharmaceutically active compound selected from the group consisting of cefuroxime axetil, cefpodoxime proxetil, amoxicillin, sumatriptan and olanzapine, comprising spraying a coating solution or suspension comprising a sugar, or a starch, or a mixture of a sugar and a starch directly onto the entire surfaces of the tablet cores without any film coating agents in the coating solution or suspension or in the tablet cores to form coated tablets, wherein no film is formed upon spray coating and wherein the resultant coating has a weight which is no more than 20% of the weight of the coated tablet.

2. A process for the coating of dispersible tablet cores, said dispersible tablet cores comprising an effective amount of at least one pharmaceutically active compound selected from the group consisting of cefuroxime axetil, cefpodoxime proxetil, amoxicillin, sumatriptan and olanzapine, comprising spraying a coating solution or suspension of a coating mixture consisting of a sugar, or a starch, or a mixture of a sugar and a starch, and optionally parting agents, pigments, colouring agents, sweeteners, flavoring agents, wetting agents, preservatives, lubricants (glidants) or antifoaming agents, directly onto the entire surfaces of the tablet cores to form coated tablets, wherein film coating agents are excluded from the tablet cores and from the coating solution or suspension wherein no film is formed upon spray coating and wherein the resultant coating has a weight which is no more than 20% of the weight of the coated tablet.

3. A coated tablet comprising a dispersible tablet core which excludes film-coating agents and includes an effective amount of at least one pharmaceutically active compound selected from the group consisting of cefuroxime axetil, cefpodoxime proxetil, amoxicillin, sumatriptan and olanzapine, coated with a coating mixture applied directly to the entire surface of the core which excludes film coating agents and which consists essentially of a sugar, or a starch, or a mixture of a sugar and a starch, and optionally parting agents, pigments, colouring agents, sweeteners, flavouring agents, wetting agents, preservatives, lubricants (glidants) or antifoaming agents wherein no film is formed upon spray coating and wherein the resultant coating has a weight which is no more than 20% of the weight of the coated tablet.

4. A dispersible tablet comprising a dispersible tablet core which comprises an effective amount of a pharmaceutically active compound selected from the group consisting of cefuroxime axetil, cefpodoxime proxetil, amoxicillin, sumatriptan and olanzapine, wherein said tablet core is coated with a coating comprising a sugar, or a starch, or a mixture of a sugar and a starch, wherein film coating agents are excluded from any part of the coated tablet core or coating thereon, no film is formed upon coating and wherein the coating comprises no more than 20% by weight of the coated tablet.

5. The process according to claim 1, wherein the pharmaceutically active compound is selected from cefuroxime axetil, cefpodoxime proxetil, amoxicillin, sumatriptan or olanzapine.

6. Coated dispersible tablets which contain an active ingredient having a bitter taste, said active ingredient selected from the group consisting of cefuroxime axetil, cefpodoxime proxetil, amoxicillin, sumatriptan and olanzapine, wherein said tablets are spray coated directly onto the entire surface thereof with one or more coating-agents selected from the group consisting of sugars, sugar derivatives, sugar alcohols, sugar alcohol derivatives, starches, starch products, starch derivatives, and starch hydrolysates, wherein film coating agents are excluded from the coated tablet cores and from the coating sprayed thereon, no film is formed upon spray coating and wherein the coating comprises no more than 20% by weight of the coated tablet.

7. A dispersible tablet comprising a dispersible tablet core which comprises an effective amount of a pharmaceutically active compound having a bitter taste, wherein said tablet core is coated with a coating comprising sugar alcohol and at least one starch-based coating agent selected from the group consisting of starches, starch products, starch derivatives, starch hydrolysates, and combinations thereof, wherein no film is formed upon spray coating, and wherein the coating comprises no more than 20% of the weight of the total weight of the coated dispersible tablet.

8. The dispersible tablet of claim 7, wherein the pharmaceutically active compound is selected from the group consisting of cefuroxime axetil, cefpodoxime proxetil, amoxicillin, sumatriptan and olanzapine, and combinations of one or more thereof.

9. The dispersible tablet of claim 7, wherein the sugar alcohol includes mannitol.

10. A process of forming a coating on a dispersible tablet core, said dispersible tablet core comprising an effective amount of at least one pharmaceutically active compound having a bitter or unpleasant taste, the process comprising:
spraying a coating solution or suspension comprising at least one sugar, or at least one starch, or a combination of the sugar and starch, and optionally parting agents, pigments, coloring agents, artificial sweeteners, flavoring agents, wetting agents, polyoxyethylene sorbitan fatty acid esters, preservatives, lubricants, and antifoaming agents dissolved or dispersed in at least one solvent onto a surface of the dispersible tablet core to form a coated dispersible tablet, wherein the coating being present in an amount to mask the bitter or unpleasant taste of the pharmaceutically active compound and in an amount of no more than 20% of the weight of the coated dispersible tablet, and wherein the coating solution is free of film-forming agents that form a film that is a barrier to the penetration of water into the dispersible tablet core and prevent the rapid disintegration of the dispersible tablet core in water when the coated dispersible tablet is immersed in water of a neutral pH at 20° C.

11. The process according to claim 10, wherein the pharmaceutically active compound is selected from the group consisting of antibiotics, antimigranes, and antiphyschotics.

12. The process according to claim 10, wherein the pharmaceutically active compound is selected from the group consisting of cefuroxime axetil, cefpodoxime proxetil, amoxicillin, sumatriptan, and olanzapine.

13. A coated dispersible tablet comprising:
a dispersible tablet core comprising an effective amount of at least one pharmaceutically active compound having a bitter or unpleasant taste; and
a coating formed on a surface of the dispersible tablet core by spraying a coating solution or suspension comprising at least one sugar, or at least one starch, or a combination of the sugar and starch, and optionally parting agents, pigments, coloring agents, artificial sweeteners, flavoring agents, wetting agents, polyoxyethylene sorbitan fatty acid esters, preservatives, lubricants, and antifoaming agents dissolved or dispersed in at least one solvent onto the surface of the dispersible tablet core, wherein the coating being present in an amount to mask the bitter or unpleasant taste of the pharmaceutically active compound and in an amount no more than 20% by weight based on the total weight of the coated dispersible tablet, and wherein the coating solution is free of film-forming agents that form a film that is a barrier to the penetration of water into the dispersible tablet core and prevent the rapid disintegration of the dispersible tablet core in water when the coated dispersible tablet is immersed in water of a neutral pH at 20° C.

14. The tablet according to claim 13, wherein the pharmaceutically active compound is selected from the group consisting of antibiotics, antimigranes, and antipsychotics.

15. The tablet according to claim 13, wherein the pharmaceutically active compound is selected from the group consisting of cefuroxime axetil, cefpodoxime proxetil, amoxicillin, sumatriptan, and olanzapine.

* * * * *